（12) United States Patent
Dovertie et al.

(10) Patent No.: US 8,476,173 B2
(45) Date of Patent: Jul. 2, 2013

(54) LAMINATE MATERIAL FOR ABSORBENT ARTICLES AND METHOD FOR ITS MANUFACTURE

(75) Inventors: Ralph Dovertie, Västra Frölunda (SE); Roy Hansson, Mölndal (SE)

(73) Assignee: SCA Hygiene Products AB, Goteborg (SE)

( * ) Notice: Subject to any disclaimer, the term of this patent is extended or adjusted under 35 U.S.C. 154(b) by 1191 days.

(21) Appl. No.: 12/085,947

(22) PCT Filed: Dec. 7, 2005

(86) PCT No.: PCT/SE2005/001855
§ 371 (c)(1),
(2), (4) Date: Jun. 3, 2008

(87) PCT Pub. No.: WO2007/067104
PCT Pub. Date: Jun. 14, 2007

(65) Prior Publication Data
US 2009/0247974 A1    Oct. 1, 2009

(51) Int. Cl.
B32B 5/26    (2006.01)
(52) U.S. Cl.
USPC ............ 442/381; 442/389; 442/392; 442/409
(58) Field of Classification Search
USPC .................................. 442/381, 389, 392, 409
See application file for complete search history.

(56) References Cited

U.S. PATENT DOCUMENTS

| | | | |
|---|---|---|---|
| 3,939,033 A | 2/1976 | Grgach et al. | |
| 4,908,026 A | 3/1990 | Sukiennik et al. | |
| 5,269,775 A * | 12/1993 | Freeland et al. | 604/385.22 |
| 6,462,253 B1 | 10/2002 | Magnusson et al. | |
| 6,468,931 B1 * | 10/2002 | Reeder et al. | 442/381 |
| 6,471,804 B1 | 10/2002 | Tennby et al. | |
| 6,783,622 B1 | 8/2004 | Backlund et al. | |
| 2002/0068150 A1 * | 6/2002 | Taneichi et al. | 428/138 |
| 2003/0050615 A1 * | 3/2003 | Sakamoto et al. | 604/358 |
| 2003/0073967 A1 | 4/2003 | Wahlstrom et al. | |

FOREIGN PATENT DOCUMENTS

| | | |
|---|---|---|
| EP | 0 685 214 A2 | 12/1995 |
| JP | 08-232149 | 9/1996 |
| JP | 2002-509816 T | 4/2002 |
| JP | 2003-527987 T | 9/2003 |
| WO | WO 97/02133 | 1/1997 |
| WO | WO 99/27879 | 6/1999 |
| WO | WO 99/49825 | 10/1999 |
| WO | WO 00/02727 | 1/2000 |
| WO | WO 00/19957 | 4/2000 |
| WO | WO 01/72253 | 10/2001 |
| WO | WO 2006/093457 | 9/2006 |

OTHER PUBLICATIONS

An English Translation of the Office Action (Notice of Reasons for Rejection) dated Jan. 18, 2011, issued in the corresponding Japanese Patent Application No. 2008-544288.
PCT/ISA/210.
PCT/ISA/237.
International Preliminary Report on Patentability and Written Opinion issued in corresponding International Patent Application No. PCT/SE2005/001855; Jun. 11, 2008; The International Bureau of WIPO, Geneva, CH.

* cited by examiner

Primary Examiner — Andrew Piziali
(74) Attorney, Agent, or Firm — Buchanan Ingersoll & Rooney PC

(57) ABSTRACT

Laminate material having a first liquid-permeable material layer and discretely-arranged material pieces of a second liquid-permeable material, wherein the material layer and the discrete material pieces are joined internally. The laminate material also has a second liquid-permeable material layer joined to the first liquid-permeable material layer and the discretely-arranged material pieces.

16 Claims, 3 Drawing Sheets

LAMINATE MATERIAL FOR ABSORBENT ARTICLES AND METHOD FOR ITS MANUFACTURE

TECHNICAL FIELD

The disclosure concerns a laminate material comprising a first liquid-permeable material layer and discretely-arranged material pieces of a second liquid-permeable material, wherein the material layer and the discrete material pieces are internally joined in discrete bonding sites. The disclosure also concerns a method for producing the laminate material.

BACKGROUND

Absorbent articles intended for single use normally have a liquid-permeable coversheet, which is intended to face the body of the user when in use. Such a coversheet is often made of a nonwoven material, i.e. a fibre cloth in which the component fibres are bonded together in a way other than weaving.

It is also known to arrange a liquid transfer layer between the coversheet and an absorbent body comprised in an article. This should have the ability to quickly receive large amounts of liquid and spread the liquid, as well as temporarily store it before it is absorbed by the underlying absorbent body. This is important, especially for the thin, compressed absorbent bodies of today, which often have a high content of highly-absorbent polymeric material, so-called "superabsorbents". The absorbent bodies of today certainly have high absorption capacity, but on the other hand, they often have a receiving speed which is too low to instantaneously cope with receiving the large amounts of liquid such as e.g. can be released upon urination in the space of a few seconds.

A porous, relatively thick liquid transfer layer, e.g. in the form of fibrous wadding, a bonded or unbonded carded fibre layer, or another type of fibre material has high instantaneous liquid-receiving capacity and can therefore temporarily store liquid until the absorbent core manages to absorb it. The same relationship also exists for many porous foam materials.

So that the absorbent article is able to receive repeated liquid volumes, it is important that the liquid transfer layer substantially manages to empty of liquid between each wetting. The open coarse capillary structure of the transfer layer thereby cooperates in a suitable fashion with the finer capillary and/or more hydrophilic absorbent body.

EP patent 0,685,214 is an example of a document which describes absorbent articles comprising a liquid transfer layer of the type described above. Further examples of documents which describe various types of liquid transfer layer are WO 99/49825 and WO 97/02133.

Documents EP 0,685,214, WO 97/02133 and WO 99/49825 also describe how liquid transfer between the outermost lying coversheet and the liquid transfer layer can be further improved. The documents describe how different coversheets and transfer layers can locally be bonded together, whereby the pore size of the liquid transfer layer is locally reduced in association with the joined areas. The reduction in pore size is a result of that, upon joining, one has also pressed the liquid transfer layer together around the joined areas. The pores in the liquid transfer layer have thereby been reduced so much that they have become smaller than the pores in the coversheet, whereby liquid moves from the coversheet to the liquid transfer layer through capillary action. Tests have also shown that effective transport of liquid stored in capillary form takes place in the coversheet in the direction of the joined areas, at the same time as liquid is emitted from the coversheet and is transported further into the liquid transfer layer around the joined areas.

This capillary effect means that only small amounts of liquid or no liquid at all, is bound in the capillaries of the coversheet, i.e. that layer which lies in contact with the skin of a user when in use. The result is an absorbent article which has an extremely dry contact surface against the skin of the wearer, after an article has received released bodily fluid from the wearer. The initially open porous structure of the liquid transfer layer is substantially maintained between the intermittently-arranged bonding areas.

It is also known to carry out intermittent joining of continuous material webs with ultrasound. For example, U.S. Pat. No. 3,939,033 describes the use of an ultrasound horn in combination with a rotating counter roller for joining continuous material webs in a particular pattern, in which the purpose of the pattern is to provide intermittent joining of the continuous material webs. The rotating counter roller comprises the pattern which is to be transferred to the laminate material which is to be joined by means of the ultrasound apparatus.

Ultrasound is an example of an especially suitable technique, as it only warms the material to be joined very locally, and leaves the remaining parts of the material unaffected by heat. Heat effects on those types of materials which are used for coversheets and liquid transfer layers affect the material in a negative way.

A well-functioning liquid transfer layer must have a certain volume so as to be able to temporarily store an instantaneous volume of liquid, which is why it is necessary that such layers have a certain thickness. On the other hand, it is not necessary that the liquid transfer layer extends across the entire surface of the absorbent article; rather it is sufficient that a necessary reception volume is located adjacent to the area of the wetting area of the absorbent article, i.e. that area which receives liquid upon use. To minimise material costs for an absorbent article, it is therefore well-known to design articles in which the liquid transfer layer only has extension in the central portions of the article in which liquid is usually received.

U.S. Pat. No. 4,908,026 describes examples of different designs, in which none of the layer covers the entire surface of the article which is intended to face the user when in use.

It is also desirable to create a liquid transfer layer which locally comprises such small pores that it preferentially absorbs liquid from a coversheet and which is furthermore arranged only in the central portions of the absorbent article, i.e. a combination of the above-described properties.

In summary, there is a desire to create a laminate comprising a substantially centrally-arranged liquid transfer layer which is joined to the coversheet in discrete bonding areas.

It is important that the discrete bonding sites between the coversheet and the liquid transfer layer are visible on the complete manufactured article, so that the absorbent article will give the user an impression of reliability. This requires that the bonding pattern should be visible from the side of the laminate which constitutes the coversheet, i.e. from that side of the laminate which is intended to face outwards when positioned on an absorbent article.

To create a visible pattern with the most commonly-occurring ultrasound technique, i.e. the technique described in U.S. Pat. No. 3,939,033, the rotating counter roller which comprises the pattern to be transferred to the laminate material must be located on the side of the laminate material from which the pattern is to be visible. The pattern is formed by pattern elements which project from the surface of the circular counter roller, whereby the pattern elements create corresponding permanent impressions in the laminate material. The rotating counter roller must therefore be positioned on the side of the laminate material comprising the coversheet, whereby the ultrasound horn must be positioned on the side of the laminate material where the liquid transfer layer is located. For laminate materials where both the coversheet and a liquid transfer layer comprise continuous material webs, this positioning of the ultrasound horn does not pose any problems.

For laminate materials in which the liquid transfer layer is formed from discrete material pieces, however, problems occur. The front edge of the discrete material pieces, i.e. that edge which is arranged forwards in the transport direction through the ultrasound apparatus, quite simply does not enter into the narrow slit between the coversheet of the laminate and the non-rotating ultrasound horn, but rather gets stuck in the slit and causes a blockage in the machinery.

In patent document WO 00/02727, one has solved this problem through stitching the front edge of each discrete material piece to the coversheet in a first reverse ultrasound operation, so as to thereby create the visible pattern in a second ultrasound operation. By the front edge of each discrete material piece is meant that edge which is oriented in the front edge of the material piece in the direction of movement.

By a first reverse ultrasound operation is meant an ultrasound operation in which the rotating counter roller is arranged on the same side of the laminate as the discrete material pieces, whereby the discrete material pieces automatically follow the rotating counter roller into the slit between the coversheet and the counter roller. In this first ultrasound operation, a substantially transverse joint is preferably provided between the coversheet and each material piece, whereby the joint is located in the front edge of each material piece in the direction of travel. In the second ultrasound operation, the discrete material pieces are located on the same side as the ultrasound horn, but as each material piece and coversheet are joined at the front edge of the material piece, no problem arises when the material piece is pressed into the narrow slit. Each discrete material piece is drawn into the slit by the continuous coversheet material. In that the counter roller comprising the desired pattern is arranged on the side of the laminate upon which the coversheet is located, the pattern will be visible from that side of the laminate which faces outwards on the complete manufactured absorbent article.

The ultrasound apparatus described in WO 00/02727 functions well, but is however unnecessarily expensive and complicated in many situations. This expensive and complicated apparatus can however be justified if the machine will primarily produce articles comprising discrete liquid transfer layers under long periods of time, without frequent changeover to different types of article.

In other machines, one wants to be more flexible and to be able to change the machine over more frequently for production of different types of article and, for instance, only manufacture absorbent articles comprising discrete liquid transfer layers or other types of discretely-arranged material layers for a short period of time.

The above-described two-step apparatus comprising one ultrasound unit for stitching the material piece and one ultrasound unit for pattern formation is both unnecessarily complicated and unnecessarily expensive for such machines. Due to the complexity of the two-step apparatus, the trimming period upon changeover to production of articles comprising liquid transfer layers is unnecessarily long and costly. Lost production volume due to long changeover times between types of article is also a negative factor for machines which are intended to alternate between different types of article. It is for instance common that one primarily produces articles without any liquid transfer layer and only provides articles with a liquid transfer layer under shorter periods.

There therefore remains a need for a laminate intended as a surface material for an absorbent article which has good liquid transfer properties and low rewet, which can be produced by an uncomplicated manufacturing process.

SUMMARY

The present disclosure provides a laminate material of the type described in the introduction, which substantially avoids the problems which have been associated with earlier known laminate materials.

The laminate material is characterized in that it comprises a first liquid-permeable material layer and a plurality of discretely-arranged material pieces of a second liquid-permeable material, wherein the material layer and the discrete material pieces are internally joined in discrete bonding sites. The laminate material is primarily characterised in that it also comprises a second liquid-permeable material layer, wherein the discretely-arranged material pieces are arranged between the first liquid-permeable material layer and the second liquid-permeable material layer. The second material layer is thereby joined to the first liquid-permeable material layer and the discretely-arranged material pieces in said discrete bonding sites. At least part of the two liquid-permeable material layers or the discretely-arranged material pieces comprises thermoplastic material, whereby the thermoplastic material has been made at least partly to soften or melt and thereby bind together the two material layers and the discretely arranged material pieces.

The laminate material has a longitudinal direction and a transverse direction, wherein the discrete material pieces are arranged at a certain distance from each other in the longitudinal direction of the laminate material.

By means of the present disclosure, one obtains a laminate material comprising discrete material pieces which can be produced in a simple fashion without risking any disturbances in production. Avoidance of disturbances in production is especially valuable as the laminate material is produced directly in a machine for absorbent articles in which every process step must be optimised with respect to reliable production.

According to one embodiment, the bonding sites of the laminate material comprise discrete points. The embodiment results in a laminate material which has an attractive pattern suitable as a pattern on an absorbent article.

According to another embodiment, the bonding sites of the laminate material comprise lines. The lines can comprise broken or continuous lines. The lines can furthermore comprise straight or curved lines. The orientation of the lines can vary within wide limits. For example, the lines can extend along or across the laminate material. Crossing lines are also possible within the scope of the embodiment.

According to one embodiment, the bonding sites of the laminate material comprise a substantially rectangular shape, and according to another embodiment, the bonding sites of the laminate material comprise a substantially circular shape.

According to one embodiment, the first liquid-permeable material layer comprises a nonwoven material, which, in accordance with one embodiment can comprise a carded, thermobonded material.

According to one embodiment, the discretely-arranged material pieces comprise fibre wadding with a thickness of 0.5-4 mm at a surface pressure of 0.02 Kpa ($20N/m^2$).

Depending on what the discretely-arranged material pieces are to be used for, it is suitable that they have an appropriate volume. The volume is determined by the thickness and surface area of each material piece.

According to one embodiment, the second liquid-permeable material layer comprises a nonwoven material, which, in accordance to a further embodiment, can comprise a carded, thermobonded material.

The laminate material, according to one embodiment, is intended as a coversheet for an absorbent article, whereby the coversheet is intended to face the user when in use.

According to one embodiment, the laminate material is intended as a coversheet for a baby diaper, and according to another embodiment, the laminate material is intended as a coversheet for an incontinence diaper.

The laminate material is especially suitable for absorbent articles which are often subjected to large volumes of urine under short periods of time. In such circumstances, the discrete material pieces of the material laminate provide a temporary storage volume, a liquid transfer layer, for the urine, before the nearby absorbent body manages to absorb the urine.

According to a further embodiment, the laminate material is intended as a coversheet for a sanitary napkin.

According to one embodiment, the discretely-arranged material pieces comprise thermoplastic material.

If the discretely-arranged material pieces also comprise thermoplastic material, the strength of the bonding in the bonding sites increases.

The disclosure further relates to a method for manufacture of a laminate material comprising continuous feeding of a first liquid-permeable material layer and a plurality of material pieces of another liquid-permeable material discretely arranged thereupon, to a bonding station. A second continuous liquid-permeable material layer is arranged on the opposite side of the discrete material pieces relative to the first liquid-permeable material layer, and the discrete material pieces are fed into the bonding station applied between the first and the second material layer. Bonding of the second material layer occurs with the first liquid-permeable material layer and the discretely-arranged material pieces in discrete bonding sites, whereby at least part of the two liquid-permeable material layers and/or the discretely-arranged material pieces comprise thermoplastic material. The thermoplastic material is made at least partly to soften or melt in the bonding station and thereby bind together the two material layers and the material pieces discretely arranged therebetween. The discrete material pieces are arranged at a certain distance from each other in the feed direction of the laminate material.

DETAILED DESCRIPTION OF THE EMBODIMENTS

Figure 1:
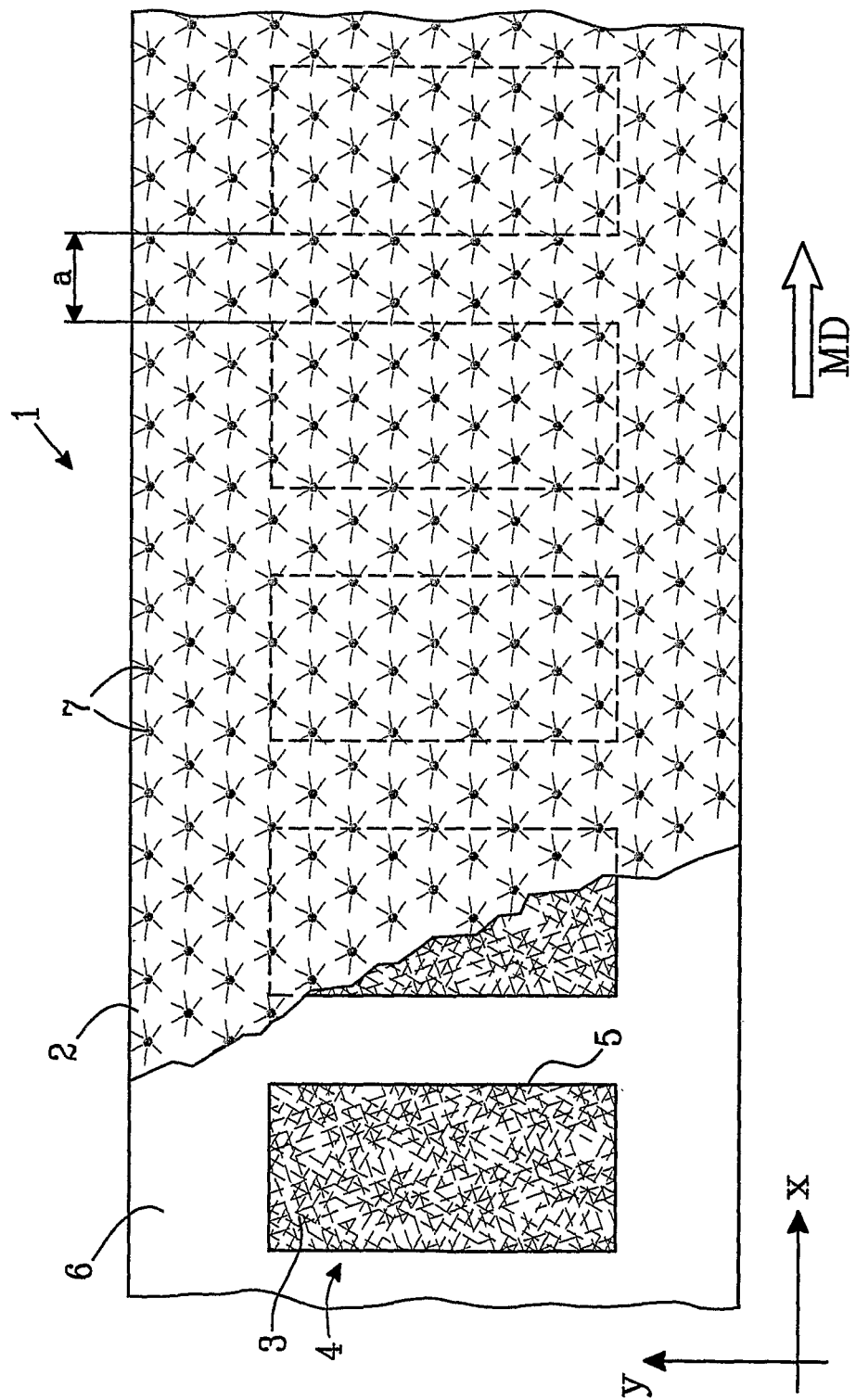
FIG. 1 shows a plan view of a material web comprising discrete liquid transfer layers.

The laminate material 1 shown in FIG. 1 comprises a first material layer 2, as well as discrete material pieces 3 intended as liquid transfer layers 4. The first material layer 2 suitably comprises a nonwoven material, preferably with a basis weight of 8-40 gram/m$^2$.

Nonwoven material can be produced through many different methods, for example, through carding or spinning of a fibre gauze which is bonded afterwards. So-called meltblown technology can also be used to deposit short fibres in the form of a fibre mat. A range of different ways of binding fibres together in a nonwoven material exist. For example, different types of binding agents can be used. Furthermore, hotmelt components in the fibres can be used for binding via ultrasound or via application of heat. Fibres comprised in a nonwoven material can be formed of so-called bi-component fibres, in which each fibre is made of two or more different types of material, whereby one of the materials melts at a lower temperature than the other in the fibre. The material with the lowest melting point makes up the material which is used for binding the final nonwoven material. Bi-component fibres in which the different component materials lie side-by-side, or fibres in which one component material is arranged as a sheath around the other component are the most commonly-occurring types of bi-component fibres. Another possible binding method for the manufacture of a nonwoven material is needling and hydroentangling. Furthermore, different binding methods can be combined with each other.

When the laminate material 1 is arranged on an absorbent article as a liquid-permeable topsheet, the first material layer 2 is the layer which is intended to face the user. It is therefore important that the first material layer 2 presents a soft and smooth surface to the user.

The liquid transfer layer 4 is preferably thicker than the first material 2 and comprises a porous, resilient fibre material with a thickness of 0.5-4 mm. The thickness is hereby the thickness of a liquid transfer layer 4 in its free state, i.e. before it is comprised in any laminate. The thickness is measured at a surface pressure of 0.02Kpa (20N/m$^2$).

When the liquid transfer layer 4 is applied to an absorbent article, each liquid transfer layer 4 should have the ability to receive large amounts of liquid in a short time, spread liquid in its plane and release liquid to an absorbent body arranged under the liquid transfer layer 4. The liquid transfer layer 4 should also be able to temporarily store the liquid which has not been absorbed by the underlying absorbent body. Resilient synthetic fibre wadding, carded bonded or non-bonded fibres layers or bulky non-woven materials are especially suitable for use as the liquid transfer layer 4. A special type of fibre material which is also suitable is a so-called tow material, with naturally substantially parallel continuous fibres. Another type of suitable material is porous, hydrophilic foam material. The liquid transfer layer 4 can also comprise two or more layers of the same or different types of material.

The liquid transfer layer 4 comprises discrete material pieces 3 and has a substantially frontward transverse edge 5. In manufacture of the laminate material 1, the front transverse edge 5 is oriented forwards in the machine direction (MD).

The laminate material 1 according to the disclosure is primarily characterised in that it comprises a second material layer 6 arranged so that the liquid transfer layer 4 is located between the first material layer 2 and the second material layer 6.

Similar to the first material layer 2, the second material layer 6 suitably comprises a nonwoven material, preferably with a basis weight of 8-40 gram/m$^2$ which is constructed and produced in the same way as the first material layer 2. Both material layers 2,6 can comprise exactly the same nonwoven material, but can also comprise different types of nonwoven material.

Figure 2:
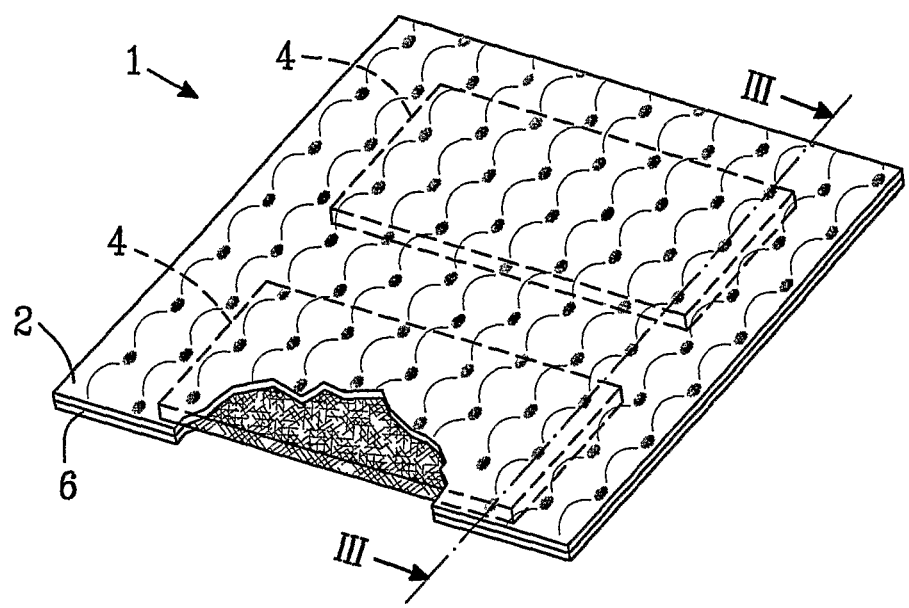
FIG. 2 shows a plan view of a laminate material according to the disclosure.

FIG. 2 shows how two specific liquid transfer layers 4 are arranged between the first material layer 2 and the second material layer 6. For ease of comprehension, parts of the material layer 2, 6 have been removed in FIG. 2.

Figure 3:
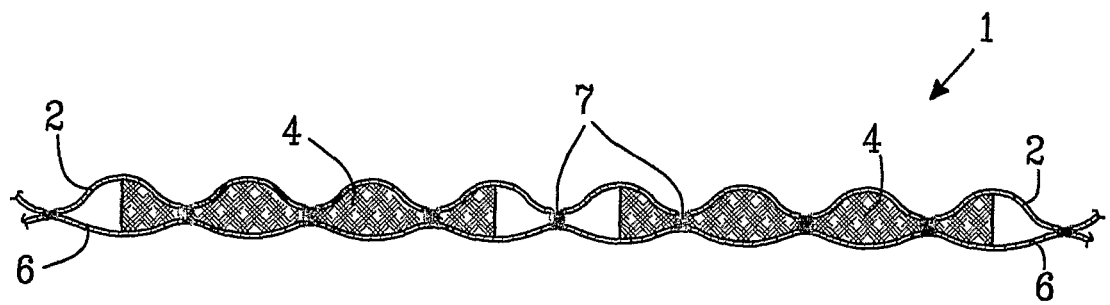
FIG. 3 shows a cross-section along the line III-III through the laminate material in FIG. 2.

FIG. 3 shows a cross-section along line III-III in FIG. 2. So as to better describe how the laminate is constructed, the thicknesses of the material layers 2, 6 and the liquid transfer layer 4 have been exaggerated in FIG. 3.

The two material layers 2, 6 and the liquid transfer layer 4 lying therebetween are internally joined in a large number of bonding sites 7. The bonding sites 7 are in the first instance points and have been formed by simultaneous compression and energy transfer to the laminate material 1.

In alternative embodiments, the bonding sites can be comprised of lines, line segments, small figures or similar.

At least part of the material layers 2, 6 comprises thermoplastic material, whereby the thermoplastic material has been made to soften or melt at the bonding sites 7 and thereby bind together the constituent components of the laminate 1. The liquid transfer layer 4 can also suitably comprise thermoplastic material which has been made to soften or melt at the bonding sites 7. Joining of the various components of the laminate 1 preferably takes place via heat bonding or by ultrasound bonding.

The bonding sites 7 are evenly-distributed over the laminate 1, but can in alternative embodiments be arranged in other ways. For instance, the bonding sites 7 can be arranged in groups over the surface of the laminate 1, wherein e.g. the distance between points in a group is less than the distance between two adjacent groups. The variation in the geometric design of each bonding site 7, as well as in the design of the location of the bonding sites over the surface of the laminate, is in principle infinite within the scope of the disclosure.

When the melted or softened thermoplastic material in the laminate 1 cools, it stiffens and serves as a binding agent, whereby the materials layers 2, 6 and 4 of the laminate material 1 are bonded together. As well as binding, a permanent local compression or concentration of the liquid transfer layer 4 is obtained. Most apparent is compression of the liquid transfer layer 4 around each bonding site 7. The compressions in the liquid transfer layer 4 mean that the capillaries of the liquid transfer layer 4 are concentrated, whereby the ability to drain the surrounding material layer 2 is improved.

As at least a part of the material layers 2, 6 comprises thermoplastic material, even those surfaces of the laminate 1 which do not comprise any liquid transfer layer have been bonded together by heat bonding or by ultrasound bonding.

In an alternative embodiment, it is possible that only the liquid transfer layer 4 comprises thermoplastic material. In such en embodiment, one must join those parts of the material layers 2, 6 which are arranged outside the liquid transfer layer 4 in an alternative way. Examples of possible joining methods are gluing or needling.

In the embodiment described, joining has occurred without any through-holes being formed at the bonding sites 7. However, the bonding sites 7 have a surface of less liquid-permeable character, whereby the degree of liquid-permeability is influenced by the amount of thermoplastic material in the bonding sites 7. In alternative embodiments, it is also plausible that the bonding sites themselves are liquid impermeable, which does not noticeably influence the liquid-receiving properties of the laminate, as the bonding sites only occupy a small part of the total surface of the laminate.

In alternative embodiments, it is possible that through-holes are created at the joining points upon joining. One possible way of providing through-holes is to increase the compression and/or energy supplied.

The laminate 1 according to the disclosure has continuous material layers 2, 6 on both sides of the liquid transfer layer 4, whereby significant benefits are obtained in the simplicity of manufacture of the laminate 1.

Figure 4:
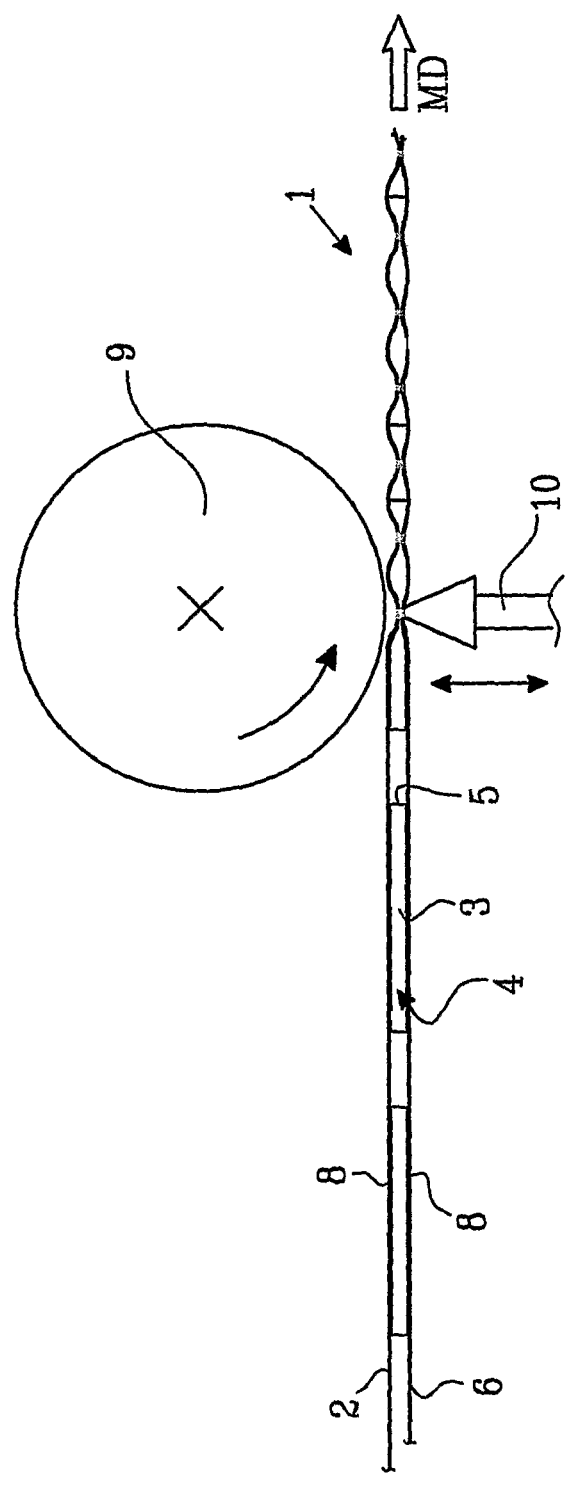
FIG. 4 shows the essence of an ultrasound process for manufacture of a laminate according to the disclosure.

FIG. 4 shows how a laminate material 1 in accordance with the disclosure is created in an ultrasound process. Unlike earlier known laminates comprising discrete liquid transfer layers 4, the outwardly-facing surface 8 of the laminate 1 lacks any transverse edges 5 in the machine direction (MD). The laminate 1 can therefore easily pass through a bonding station without any of the front edges 5 of the liquid transfer layers 4 getting stuck and causing a blockage in the bonding process. The disclosure is especially advantageous when ultrasound technology is used to join the layers of the laminate 1. As described above, ultrasound technology involves that a rotating pattern roller 9 is arranged on the side of the laminate 1 from which the bonding pattern should be most clearly visible and that an ultrasound horn oscillating in the thickness direction of the laminate material 1 is arranged on the opposite side of the laminate 1.

As described above, the bonding pattern is intended to face the user when the laminate material 1 is applied to an absorbent article, i.e. on the outside of the absorbent article.

In alternative embodiments, it may of course be possible to apply the laminate material 1 with the patterned face oriented in against the absorbent body of the absorbent article, but the pattern will not be so clearly noticeable on the absorbent article. A certain risk with this alternative embodiment is also that small air pockets arise between the absorbent core and the impressions in the laminate material 1 (see FIG. 3), whereby the liquid transfer between the laminate material 1 and the underlying absorbent body may be slightly disturbed.

In that the continuous material layers 2, 6 pass both the pattern roll and the ultrasound horn, the manufacturing process is not critical as regards a discrete material piece 3 getting stuck and causing a blockage in the inlet between the pattern roll 9 and the ultrasound horn 10.

The laminate 1 according to the disclosure also provides more reliable operation of the manufacturing process upon lamination with two opposing warm rotating bonding rollers. The advantages of this laminating procedure are however not as great as lamination with ultrasound.

It is common that the manufacture of the laminate 1 according to the disclosure occurs as a process step in a machine for the production of baby diapers, incontinence articles, sanitary napkins or other absorbent articles. Such machines comprise a large number of process steps, such that it is of utmost significance to minimise the risk of disturbances in production in each process step. These machines often run at very high speeds and each production stoppage requires that time-consuming and complicated start-up procedures must be carried out. Besides lost production volume, unnecessary production stoppages also mean that a large amount of material is wasted.

The disclosure also includes all possible combinations of the described embodiments.

Furthermore, the disclosure is not limited to the above-named embodiments, but is of course suitable for other embodiments within the scope of the following claims.

The invention claimed is:
1. A laminate material comprising a first liquid-permeable material layer, a plurality of discretely-arranged material pieces of a second liquid-permeable material and a second liquid-permeable material layer,
   wherein the first material layer and the discrete material pieces are internally joined in discrete bonding sites, wherein the discretely-arranged material pieces are arranged between the first liquid-permeable material layer and the second liquid-permeable material layer, wherein the second material layer is joined to the first liquid-permeable material layer and the discretely-arranged material pieces in said discrete bonding sites, wherein at least part of the two liquid-permeable material layers and/or the discretely-arranged material pieces comprises thermoplastic material, whereby the thermoplastic material has been made at least partly to soften or melt and thereby bind together the two material layers and the material pieces discretely arranged therebetween, wherein the discrete material pieces are arranged at a distance from each other in the longitudinal direction of the laminate material, wherein the first liquid-permeable material layer comprises a nonwoven material, wherein the second liquid-permeable material layer comprises a nonwoven material.

2. The laminate material according to claim 1, wherein the bonding sites comprise discrete points.

3. The laminate material according to claim 1, wherein the bonding sites comprise lines.

4. The laminate material according to claim 1, wherein the bonding sites have a substantially rectangular shape.

5. The laminate material according to claim 1, wherein the bonding sites comprise a substantially circular shape.

6. The laminate material according to claim 1, wherein the nonwoven material is a carded, thermobonded material.

7. The laminate material according to claim 1, wherein the discretely-arranged material pieces comprise fibre wadding with a thickness of 0.5-4 mm at a surface pressure of 0.02 Kpa ($20N/m^2$).

8. The laminate material according to claim 1, wherein the nonwoven material is a carded, thermobonded material.

9. The laminate material according to claim 1,
wherein the discrete material pieces are arranged at a distance from each other in the longitudinal direction of the laminate of at least 5 mm.

10. The laminate material according to claim 1, wherein the discretely-arranged material pieces comprise thermoplastic material.

11. An absorbent article comprising a coversheet adapted to face a user when in use, the coversheet being the laminate material of claim 1.

12. The laminate material according to claim 1,
wherein only the discretely-arranged material pieces comprise the thermoplastic material, and the two liquid-permeable material layers are free of a thermoplastic material.

13. The absorbent article according to claim 11, wherein the absorbent article is a baby diaper.

14. The absorbent article according to claim 11, wherein the absorbent article is an incontinence diaper.

15. The absorbent article according to claim 11, wherein the absorbent article is a sanitary napkin.

16. The absorbent article according to claim 11,
wherein the first or the second material layer forms a topsheet facing the user and each of the discretely-arranged material pieces form a liquid-transfer layer.

* * * * *